United States Patent [19]

Taylor et al.

[11] 3,991,193

[45] Nov. 9, 1976

[54] DERIVATIVES OF 4(3H)-QUINAZOLONE, PHARMACEUTICAL COMPOSITIONS THEREOF AND METHODS OF USE

[75] Inventors: John Bodenham Taylor, Down Ampley; Derek Ralph Harrison, Swindon, both of England

[73] Assignee: Roussel-UCLAF, Paris, France

[22] Filed: Sept. 25, 1975

[21] Appl. No.: 616,645

Related U.S. Application Data

[62] Division of Ser. No. 516,779, Oct. 21, 1974, Pat. No. 3,928,354.

[30] Foreign Application Priority Data

Oct. 23, 1973 United Kingdom............... 49338/73

[52] U.S. Cl. ............................................... 424/251
[51] Int. Cl.² ........................................ A61K 31/505
[58] Field of Search............... 424/251; 260/251 QA Primary Examiner—Stanley J. Friedman
Attorney, Agent, or Firm—Bacon & Thomas

[57] ABSTRACT

A derivative of 4(3H)-quinazolone, its method of preparation, and pharmaceutical compositions are described. In particular, 2-methyl-3-(o-cyanophenyl)-4(3H)-quinazolone and its acid addition salts are described. This compound may be prepared by the reaction of N-acetylanthranilic acid with anthranilonitrile in the presence of a dehydrating agent. The quinazolone and its salts possess pharmacological activity.

7 Claims, No Drawings

DERIVATIVES OF 4(3H)-QUINAZOLONE, PHARMACEUTICAL COMPOSITIONS THEREOF AND METHODS OF USE

This is a division of application Ser. No. 516,779, filed Oct. 21, 1974, now U.S. Pat. No. 3,928,354.

The present invention relates to a derivative of 4(3H)-quinazolone (3,4-dihydroquinazolin-4-one), a process for preparing same, and a pharmaceutical composition. The derivatives according to the present invention is 2-methyl-3-(o-cyanophenyl)-4(3H)-quinazolone of the formula I:

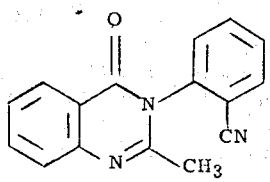

and its acid addition salts.

The acid addition salts may be derived from inorganic or organic acids, in particular from mineral acids such as hydrochloric, hydrobromic, nitric, sulphuric or phosphoric acid. The organic acids include organic carboxylic acids such as acetic, formic, benzoic, maleic, fumaric, succinic, tartaric, citric, oxalic, benzilic, glyoxylic, and aspartic acid; and organic sulphonic acids such as alkanesulphonic and arylsulphonic acids, e.g. methane sulphonic acid and p-toluenesulphonic acid. 2-Methyl-3-(o-cyanophenyl)-4(3H)-quinazolone hydrochloride is the particularly preferred salt.

The quinazolone and its pharmaceutically acceptable acid addition salts have been found to possess pharmacological activity. Such pharmacological activity includes, in particular, hypnotic sedative and anticonvulsant activity, and a further feature of the present invention are pharmaceutical compositions containing 2-methyl-3-(o-cyanophenyl)-4(3H)-quinazolone or an acid addition salt thereof together with a pharmaceutical carrier or excipient. Such compositions may be used in the treatment of insomnia, anxiety, irritability, hyperemotivity and neurotic conditions in man and animals. The dose will vary with the type site of administration, the particular condition being treated, the compound used and the subject. However, a typical range for the daily dose per os may be from 5 to 500 mg.

These compositions may be presented in any convenient form for oral, parenteral or rectal administration, e.g. tablets, coated tablets, capsules, granules, suppositories and injection solutions, prepared by conventional methods and containing conventional carriers and excipients, e.g. talc, gum arabic, lactose, starch, magnesium stearate, cocoa butter, aqueous or nonaqueous vehicles, animal and vegetable oils and fats, paraffin derivatives, glycols, wetting, dispersing and emulsifying agents and preservatives.

2-Methyl-3-(o-cyanophenyl)-4(3H)-quinazolone and acid addition salts thereof may be prepared by any conventional method, but a particularly preferred method which is a further feature of the present invention comprises reacting N-acetylanthranilic acid with anthranilonitrile in the presence of a dehydrating agent. The dehydrating agent is preferably a phosphorus halide, advantageously phosphorus trichloride, pentachloride or oxychloride. The reaction is preferably effected in an inert organic solvent, in particular, an aromatic hydrocarbon such as toluene, xylene, or benzene.

The reaction is advantageously effected at the boiling point of the reaction mixture under reflux, and then cooled. The product precipitates from the cooled reaction mixture and may be purified by treatment with alkali, such as a sodium bicarbonate solution and then extracted with an organic solvent such as chloroform.

The acid addition salts may be prepared by reacting stoichiometrical proportions of the desired acid and the free base. Salts may also be prepared from existing salts by anion exchange techniques.

The following Examples illustrate the invention.

EXAMPLE 1

2-Methyl-3(o-cyanophenyl)-4(3H)-quinazolone and its hydrochloride

Phosphorus trichloride (16 ml) in toluene (100 ml) was added over 15 minutes to anthranilonitrile (40 g) and N-actylanthranilic acid (60g) in toluene (500 ml) stirred under reflux. The mixture was stirred under reflux for 3 hours, cooled and the precipitate filtered off. The precipitate was neutralised with a saturated sodium bicarbonate solution, extracted with chloroform and the extracts washed with water. Evaporation of the dried extracts gave a pale yellow solid which was crystallised from methanol to give colourless crystals of 2-methyl-3-(o-cyanophenyl)-4(3H)-quinazolone (36g, 41%), m.p. 165°–6°;ir: 2235 (C ≡ N), 1700 (C=O) cm$^{-1}$; nmr $\tau$ (CDCl$_3$) 1.71 (1H, $d$, J 7Hz, .5—H), 2.1–2.8. (7H, $m$, ArH), 7.78 (3H, $s$, 2—Me).

Anal. Calcd. for $C_{16}H_{11}N_3O$ : C, 73.55; H, 4.24; N, 16.08. Found: C, 73,52; H, 4.56; N, 15.84%.

Addition of hydrogen chloride in ether to a solution of the quinazolone im methylene chloride gave colourless crystals of 2-methyl-3-(o-cyanophenyl)-4(3H)-oxo quinazolinium hydrochloride, m.p. 165°–75°; ir: 2300 (broad) (NH), 2240 (C ≡ N), 1730 (C=O) cm$^{-1}$; nmr $\tau$ ($d_6$DMSO) 1.7.2.4. (8H, $m$, ArH), 7.70 (3H, $s$, 2—Me).

Anal. Calcd. for $C_{16}H_{12}N_3Clo$ : C, 64.54; H, 4.03; N, 14.11; Cl, 11.96%. Found: C, 64.30; H, 4.32; N, 13.73; Cl, 12.24%.

EXAMPLE 2

Tablets were prepared which corresponded to the formula:

| | | |
|---|---|---|
| a) | 2-methyl-3-(o-cyanophenyl)-4(3H)-quinazolone hydrochloride | 50 mg |
| | Excipient q.s. for 1 tablet | 200 mg |
| (Excipient: lactose, starch, talcum and magnesium stearate). | | |
| b) | 2-methyl-3-(o-cyanophenyl)-4(3H) quinazolone | 50 mg |
| | excipient q.s. for 1 tablet | 200 mg |
| (Excipient: as for (a)) | | |

Pharmacological study

1. The activity of 2-methyl-3-(o-cyanophenyl)-4(3H)-quinazolone hydrochloride was investigated in the mouse by the following 5 tests.

1. Righting Reflex Test

Groups of ten mice received the test compound orally or i.p. at various dose levels, a control group receiving vehicle alone. All mice were housed individually in glass beakers and were assessed for loss of righting reflex at ¼, ½, 1, 2, 4 and 6 hours after dosing. A positive response was recorded if the mouse failed to regain righting reflex during a 30 sec. observation. From the results obtained a dose response line was constructed and the dose producing 50% loss of righting reflex was estimated for each observation time. This $ED_{50}$ value (the dose producing loss of righting reflex in 50% of a group of mice) was quoted for the time of peak activity. Results appear in table 1.

2. Rotating Drum Test

Groups of ten mice received p.o. or i.p. the test compound at various dose levels, a control group receiving the vehicle alone by each route .30 min. after dosing each group of mice was placed on a 30 cm diameter rotating drum revolving at 1 revolution/minute. The mice were placed on the drum against its direction of movement and the number of mice falling off within a 2 min. test period was noted. From the results obtained a dose response line was constructed and the dose causing 50% of the mice to fall off the drum ($ED_{50}$) was estimated. Results appear in table 1.

3. Anticonvulsant Test Against Electroshock

Groups of ten mice received p.o. or i.p. the test compound at various dose levels, a control group received the vehicle alone. 30 min. after dosing, each group was then shocked via auricular electrodes using the electroshock apparatus (Ugo Basile ECT apparatus for small mammals) using the following parameters:

| | |
|---|---|
| Pulse width | 0.2 ms |
| Frequency | 100 Hz |
| Pulse duration | 0.2 s |
| Current | 55 mA |

The number of mice which underwent tonic extension of hind limbs was noted. The dose protecting 50% of the mice ($ED_{50}$) was estimated.
Results appear in table 1.

4. Potentiation of Hexobarbitone Sleeping Time

A group of eight control mice received a dose of 65 mg/kg Hexobarbitone Sodium i.v. and subsequent sleeping times were recorded. A time value equivalent to mean sleeping time plus two standard deviations was established as a cut-off point. Other groups of eight mice received in identical dose of Hexobarbitone Sodium and at half the means control sleeping time were given various doses of the test compound i.p. The number of mice in each group asleep at the cut-off was recorded. A dose response curve was constructed and the dose at which 50% of the mice remained asleep at this cut-off point ($ED_{50}$) was estimated. Results appear in table 1.

5. Acute Toxicity Tests

Acute toxicities by p.o and i.p. routes were conducted using groups of ten mice at various dose levels. Groups dosed p.o. and i.p. were assessed for mortality at 24 hours. Results appear in table 1.

The activity of methaqualone (2-methyl-3-(o-tolyl)-4-quinazolone) was investigated under the same conditions by using the test procedures indicated in the five tests above. These results appear in table 1.

Table 1

| Tests | $ED_{50}$ (Doses in mg/Kg) | | | |
|---|---|---|---|---|
| | 2-methyl-3-(o-cyanophenyl)-4(3H)-quinazolone, HCl | | Methaqualone (2-methyl-3-(o-tolyl-4(3H)-quinazolone) | |
| Righting Reflex | i.p. | 47 | i.p. | 81 |
| Test in Mouse | p.o. | 112 | p.o. | 160 |
| Rotating Drum | i.p. | 26.5 | i.p. | 30 |
| Test in Mouse | p.o. | 23.0 | p.o. | 49 |
| Anticonvulsant Test Against Electroshock in Mouse | i.p. | 10 | i.p. | 21.5 |
| | p.o. | 9 | p.o. | 42 |
| Potentiation of Hexobarbitone Sleeping Time in Mouse | i.p. | 9.0 | i.p. | 25 |
| Acute Toxicity | $LD_{50}$ i.p. = 570 | | $LD_{50}$ i.p. = 550 | |
| | $LD_{50}$ p.o. = 1600 | | $LD_{50}$ p.o. = 1700 | |

These results show that 2-methyl-3-(o-cyanophenyl)-4(3H)-quinazolone hydrochloride is a very effective oral hypnotic in mouse, with a better therapeutic ratio than Methaqualone.

II. The activity of 2-methyl-3-(o-cyanophenyl)-4(3H)-quinazolone hydrochloride was also investigated in rat by the following tests.

1. Righting Reflex Test

Groups of ten male Sprague-Dawley rats received the test compound i.p. or p.o. at various doses. The animals dosed i.p. were assessed for loss of righting reflex immediately after dosing and those dosed p.o. were assessed at ¼, ½, 1, 2, 4 and 6 hours after dosing. $ED_{50}$ values were estimated as for the Righting Reflex Test in the mouse and are shown in table 2.

2. Acute Toxicity Test

Groups of ten rats were dosed p.o. or i.p. with various doses of the test compound and after 24 hours were assessed for mortality. Results appear in table 2.

The activity of Methaqualone was investigated in the same conditions. Results appear in table 2 below.

Table 2

| Tests | $ED_{50}$ (Doses in mg/Kg) | | | |
|---|---|---|---|---|
| | 2-methyl-3-(o-cyanophenyl)-4(3H)-quinazolone, HCl | | Methaqualone | |
| Righting Reflex | i.p. | 28 | i.p. | 48 |
| Tests in Rat | p.O. | 106 | p.o. | 170 |
| Acute Toxicity | $LD_{50}$ i.p. | >300 | $LD_{50}$ i.p. | 190 |

Table 2-continued

| Tests | ED₅₀ (Doses in mg/Kg) | |
| --- | --- | --- |
| | 2-methyl-3-(o-cyano-phenyl)-4(3H)-quinazolone, HCl | Methaqualone |
| Test in Rat | LD₅₀ p.o. >1000 | LD₅₀ p.o. 440 |

These results show that 2-methyl-3(o-cyanophenyl)-4(3H)-quinazolone hydrochloride is less toxic, and much more effective than Methaqualone in the rat.

What is claimed is:

1. A method of treating insomnia, anxiety, irritability, hypermotivity and neurotic conditions comprising administering to men or animals an effective amount of a compound selected from the group consisting of 2-methyl-3-(o-cyanophenyl)-4(3H)-quinazolone of the formula I:

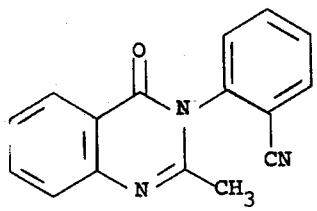

I and a pharmaceutically acceptable acid addition salt thereof.

2. The method of claim 1 wherein the acid addition salt is formed from an acid selected from the group consisting of the hydrochloric, hydrobromic, nitric, sulphuric, phosphoric, acetic, formic, benzoic, maleic, fumaric, succinic, tartaric, citric, oxalic, benzilic, glyoxylic, aspartic, methane suphonic and p-toluenesulphonic acids.

3. The method of claim 2 wherein the acid addition salt is the hydrochloride.

4. The method of claim 1 wherein the effective amount of said compound is administered as a daily dose per os of from 5 to 500 mg.

5. Pharmaceutical compositions comprising an effective amount of a compound selected from the group consisting of 2-methyl-3-(o-cyanophenyl)-4(3H)-quinazolone of the formula I:

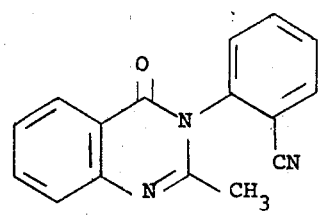

I and a pharmaceutically acceptable acid addition salt thereof; and a pharmaceutical carrier.

6. The pharmaceutical composition of claim 5 wherein the acid addition salt is formed from an acid selected from the group consisting of hydrochloric, hydrobromic, nitric, sulphuric, phosphoric, acetic, formic, benzoic, maleic, fumaric, succinic, tartaric, citric, oxalic, benzilic, glyoxylic, aspartic, methane sulphonic and p-toluenesulphonic acid.

7. The pharmaceutical composition of claim 6 which is the hydrochloride.

* * * * *